United States Patent [19]

Cullen et al.

[11] Patent Number: 5,321,764

[45] Date of Patent: Jun. 14, 1994

[54] IDENTIFICATION OF WHEAT CULTIVARS BY VISUAL IMAGING

[75] Inventors: Andra J. Cullen, Glenview, Ill.; Russell C. Hoseney; Jon M. Faubion, both of Manhattan, Kans.

[73] Assignee: Kansas State University Research Foundation, Manhattan, Kans.

[21] Appl. No.: 818,830

[22] Filed: Jan. 10, 1992

[51] Int. Cl.$^5$ .................. G06K 9/48; G06K 9/46; G06K 9/62; B07C 5/00

[52] U.S. Cl. .................. 382/1; 382/8; 382/22; 382/25; 382/36; 382/39; 209/576; 209/939; 364/554; 364/555; 364/577; 348/135

[58] Field of Search .................. 382/8, 1, 22, 25, 26, 382/36, 39; 358/101, 107; 209/586, 576, 659, 939; 364/554, 555, 560, 577; H04N 7/00, 7/18

[56] References Cited

U.S. PATENT DOCUMENTS

| | | | |
|---|---|---|---|
| 4,115,803 | 9/1978 | Morton | 358/107 |
| 4,687,107 | 8/1987 | Brown et al. | 209/556 |
| 4,818,380 | 4/1989 | Azegami et al. | 209/565 |
| 4,963,035 | 10/1990 | McCarthy et al. | 382/28 |
| 4,975,863 | 12/1990 | Sistler et al. | 364/555 |

OTHER PUBLICATIONS

Bietz, J. A. 1983, "Separation of cereal proteins by reversed-phase high-performance liquid chromatography," J. Chromatogr. 255:219-238.

Chen, C. Y., Skarsaune, S. K. and Watson, C. A. 1972, "Relation of kernel color to wheat class and grade," Cereal Science Today vol. 17, No. 11, pp. 340-343.

Edison, A. R. and Brogan, W. L. 1972. Size measurement statistics of kernels of six grains. Paper #72-841. ASAE.

Goodman, D. E. and Rao, R. M. 1984, "A new, rapid, interactive image analysis method for determining physical dimensions of milled rice kernels," J. Food Sci. 49:648-649.

Jones, B. L., Loookhart, G. L., Hall, S. B. and Finney, K. F. 1982. "Identification of wheat cultivars by gliadin electrophoresis: Electrophoregrams of the 88 wheat cultivars most commonly grown in the United States in 1979", Cereal Chem. vol. 59, No. 3, pp. 181-188.

Lookhart, G. L. and Pomeranz, Y. 1985b. Gliadin high-performance liquid chromatography and polyacrylamide gel electrophoresis patterns of wheat grown with fertilizer treatments in the United States and Australia on sulfur-deficient soils. Cereal Chem. vol. 62, No. 3, pp. 227-229.

Meppelink, E. K. 1974. Untersuchungen uber kie methodik der kornhartebestimmung bei weizen gertreide. Mehl Brot. 28:142. [now translated as "Investigations on the Methodology of Measuring the Hardness of Wheat Kernels"].

(List continued on next page.)

[57] ABSTRACT

A method for identifying wheat cultivars is provided which employs an imaging device such as a video camera and a computer to acquire and process images of grain samples and to identify the particular type or cultivar of the wheat by the images obtained thereby. The method involves the steps of acquiring the image of the kernel and germ for each grain, processing the image into digital format, storing data in the computer corresponding to the edge of the kernel and germ, determining the image characteristics of the kernel and germ, and comparing the image characteristics for the sample to a known standard. By accumulating data for a number of grains, calculating statistical information for the sample, and comparing to a known standard, the particular cultivar of the sample may be identified.

71 Claims, 9 Drawing Sheets

OTHER PUBLICATIONS

Neuman, M., Saperstein, H. D., Shwedyk, E., and Bushuk, W. 1987. Discrimination of wheat class and variety by digital image analysis of whole grain samples. J. of Cereal Sci. 6:125–132.

Obushowski, W. and Bushuk, W. 1980a. Wheat hardness: Comparison of methods of its evaluation. Cereal Chem. vol. 57, No. 6, pp. 421–425.

Rehkugler, G. E. and Throop, J. A. 1985, "Apple sorting with machine vision, Paper 85-3543", ASAE.

Schmalzfried, T. E. 1985, "Identification of wheat varieties using machine vision", Master's thesis, Kansas State University, Manhattan, Kans.

Simmonds, D. H. Oct. 1974, "Chemical basis of hardness and vitreosity in the wheat kernel", Baker's Digest 48:16.

Symes, K. J. 1961, "Classification of Australian wheat varieties based on granularity of their wholemeal", Aust. J. Exp. Agr. Animal Husb. 1:17–23.

Trombly, J. 1987. Applications of machine vision in the food industry. 62nd Annual Technical Conference of the Biscuit Bakers Institute, Feb. 1987, Chicago, Illinois.

Zayas, I., Lai, F. S., and Pomeranz, Y. 1986. Discrimination between wheat classes and varieties by image analysis. Cereal Chem. 63:52–56.

Zayas, I., Pomeranz, Y., and Lai, F. S. 1985, "Discrimination between Arthur and Arkan wheats by image analysis," Cereal Chem. 62(6):478–480.

*Primary Examiner*—David K. Moore
*Assistant Examiner*—Michael Cammarata
*Attorney, Agent, or Firm*—Hovey, Williams, Timmons & Collins

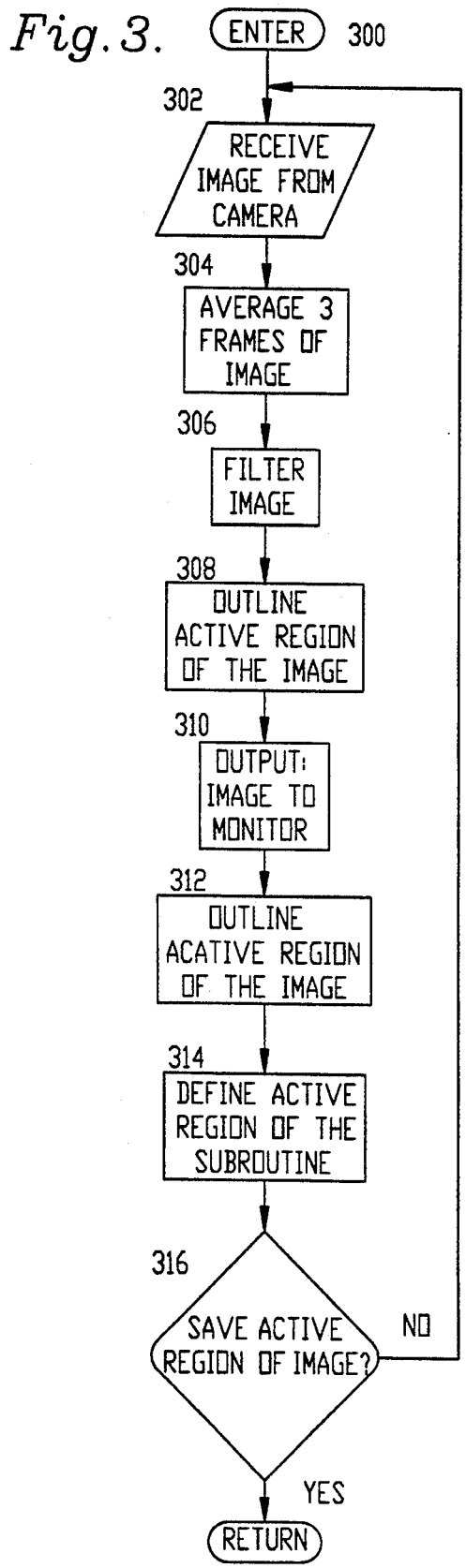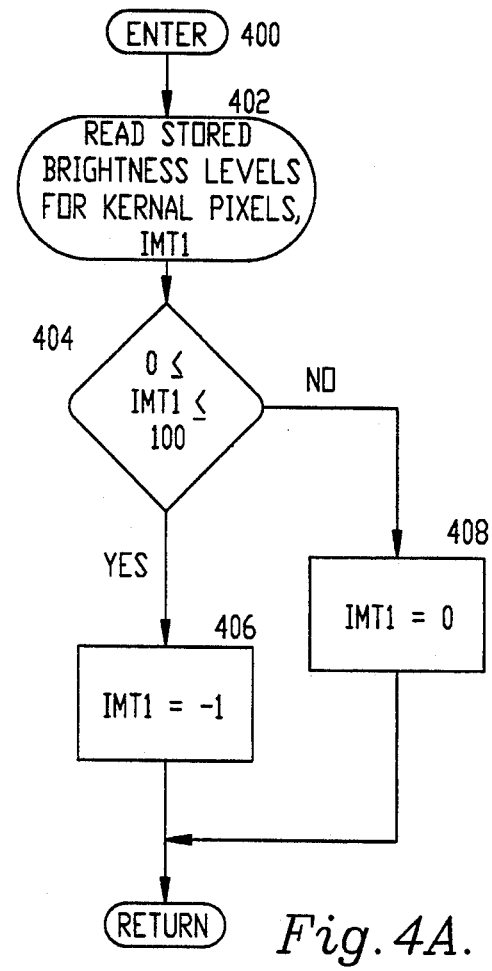
Fig. 3.
Fig. 4A.

IDENTIFICATION OF WHEAT CULTIVARS BY VISUAL IMAGING

A microfiche appendix containing the source code of a computer program useful in accordance with the present invention is appended hereto as a single microfiche containing 54 frames.

BACKGROUND OF THE INVENTION

1. Field of the Invention

This invention relates to a method for identifying varieties of wheat or other grains by visual imaging and comparison of the characteristics of a sample thereof to a known standard. The method involves the use of a series of steps advantageously employing a computer to conduct digital image analysis of the kernel and germ in order to correctly identify the cultivar of the particular sample.

2. Description of the Prior Art

Even those largely unfamiliar with the agriculture industry recognize that wheat and other grains are further differentiated by classes and cultivars. Classes of wheat such as Hard Red Spring Wheat, Hard red Winter Wheat, Soft Red Winter Wheat and White are planted in different regions at different times, used for different purposes and command different prices at the elevator and at commodities exchanges. Within each class, a variety of different cultivars have been developed, each with its own characteristics and properties. For example, Bounty, Centura, Centurk, Mustang, Newton, Tam 105, Pike and Rough Rider are Hard Red Winter (HRW) wheat cultivars and Katepaw, Stoa, and Len are Hard Red Pring (HRS) wheat cultivars while Hill, Stephans and Lewjain are examples of White wheat cultivars. There are presently over 600 cultivars of wheat grown in the United States.

It is obviously necessary to identify the different cultivars in order to properly classify the wheat for purposes such as sale to a miller or use as seed. The responsibility for wheat classification traditionally falls to Federal Grain Inspection Service (FGIS) inspectors which are to check a representative sample of the wheat to determine the cultivar by such characteristics as brush size, germ angle, cheek angle, kernel shape, and seed coat texture. The FGIS personnel are charged with knowing the characteristics of all varieties handled within their particular market. However, the proliferation of new cultivars and the practice of crossbreeding varieties has nearly overwhelmed the capabilities of the FGIS. The current method of wheat classification, developed in 1917, is somewhat archaic and obsolete in view of the number of new variety releases each year. Thus, there is a genuine need for a rapid, accurate, more efficient and precise procedure of kernel classification and identification.

Previous studies have attempted to use kernel color as a separation method by such techniques as scanning spectrophotometry. Other efforts have employed kernel hardness, but the results are difficult to reproduce. Still other proposed methods have used electrophoresis or chromatography to isolate and characterize cereal proteins constituencies.

Attempts to identify food products by seed shape and size parameters have also been employed. These have encountered certain methodological limitations, while further studies have employed digital image analysis to study the physical dimensions of cereal crops such as rice and wheat. However, the results of these image analyses indicated that discrimination between class and cultivar were limited in terms of number of kernel characteristics used to discriminate between the classes. It thus appears that new discriminators must be employed to handle identification and classification in an efficient manner.

SUMMARY OF THE INVENTION

These problems are in large part solved by the present invention which enables positive identification of grain samples according to parameters established by comparison with known standards. Even a sample comprised of numerous individual kernels taken from two separate cultivars may be detected. The present invention obtains an image of each of the kernels in the sample and from that image determines the length and breadth of the kernel and germ, perimeter and area of each, ratio therebetween and other objective discriminators from which a positive identification can be made by matching the sample image data to similar edge data discriminators for a known cultivar.

A computer is coupled to a video camera which acquires the images. The images are converted from the videocamera analog output to digital format and the edge of each kernel, as well as the edge of the germ thereof, are determined from the brightness of the acquired image. The computer then performs a series of calculations and operations which yield edge data representative of the peripheral edge of the kernel and germ from which such characteristics as area, perimeter, length and breadth can be determined. Once the characteristics have been determined and ratio calculations for other discriminators derived from these characteristics are complete, the objective data is compared to a known standard. A library of grain edge discriminators for known cultivars is used as a standard for matching against the discriminators for the grain sample to enable the computer to identify the sample. Because each kernel may vary somewhat from the norm of a particular cultivar, a number of kernels typically comprise the sample. In preferred embodiments of the invention, a statistical analysis yielding an average or norm and a range comprising a predetermined number of standard deviations is employed to identify the sample as a whole.

In the preferred embodiments of the method hereof, the invention utilizes the computer to present a distinct image for each kernel and eliminates surface anomalies form the digitized image. That is to say, if a kernel presents an irregular surface due to broken fragments, inclusions, or projections, the computer employs specific subroutines which compensate for the irregularities. The image is thus resolved or "cleaned" by the computer to enable identification of the grain kernel as if it were it absent of such irregularities.

BRIEF DESCRIPTION OF THE DRAWINGS

FIG. 3 is a computer program flowchart of the image acquisition subroutine of the present invention;

FIG. 4A is a computer program flowchart of the kernel thresholding subroutine of the present invention;

DESCRIPTION OF THE PREFERRED EMBODIMENT

Figure 1:
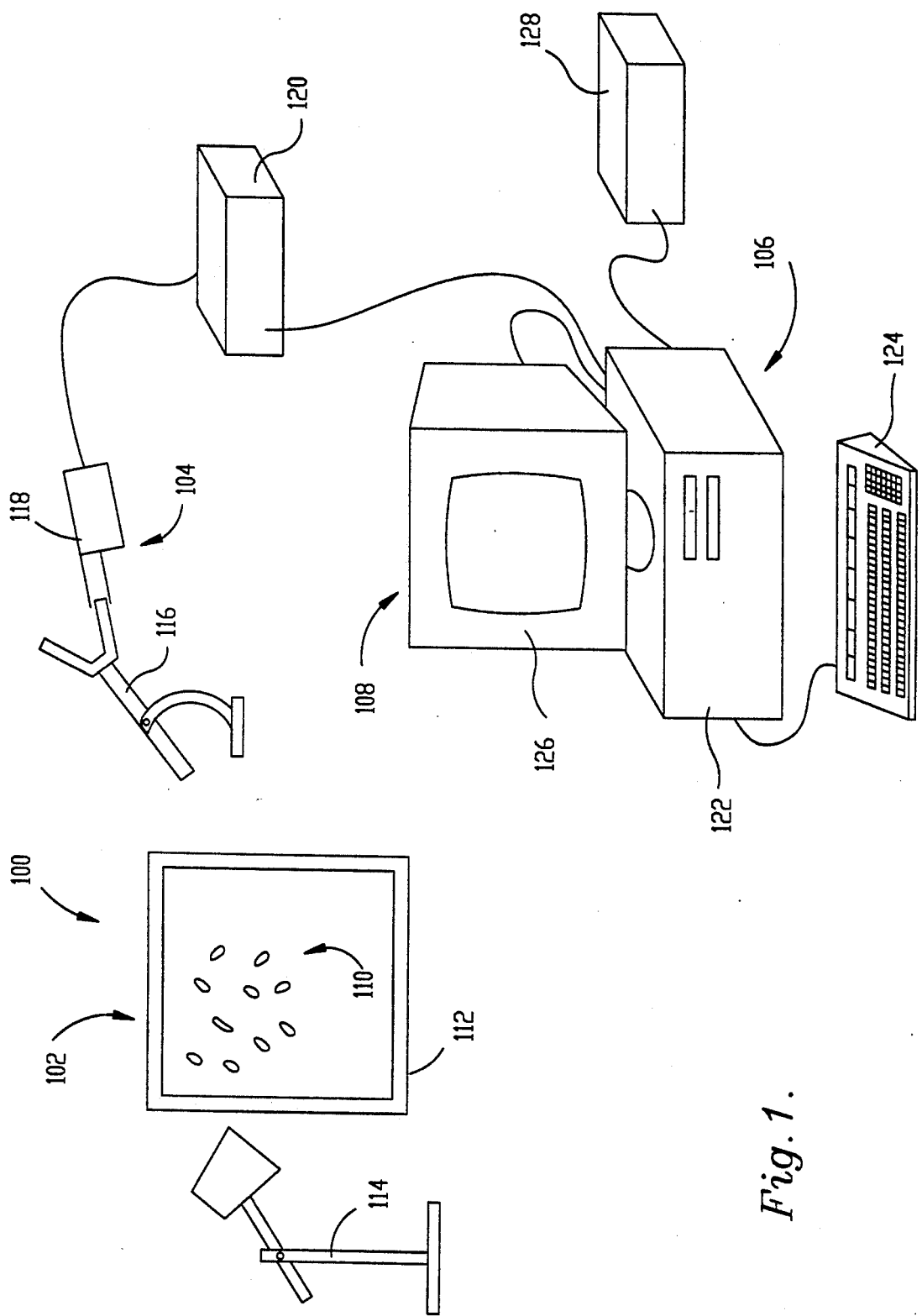
FIG. 1 is a diagrammatic view of the hardware components useful in accordance with the present invention.

Referring now to FIG. 1, a grain identification apparatus 100 broadly includes lighting apparatus 102, image acquisition apparatus 104, data processing apparatus as well as data output apparatus 108 for displaying information to the operator. The gain identification apparatus is used to identify a sample of grain 110. To provide adequate statistical information, preferably about 100 kernels, each having a germ therewithin, make up each sample 110.

In greater detail, lighting apparatus 102 includes a light table 112 and an overhead lamp 114 for illuminating the grain sample 110 consisting of a number of kernels of grain such as wheat. Because the germ within each kernel must be sufficiently illuminated to present a detectable image, backlighting from the light table 112 as well as overhead lighting from the lamp 114 are preferred to obtain a recognizable image for both the germ and the surrounding kernel for the sample.

The image of each kernel is acquired by image acquisition apparatus 104 which includes a microscope 116 and a video camera 118. A microscope 116 found useful in the invention hereof is a Wild M-5 manufactured by Wild Heerburg of Switzerland and has a Y-shaped viewing tube which permits the operator to acquire the image of the desired kernel by looking through one lens and the video camera 118 to be coupled to the other lens. A video camera 118 found useful in the invention is a Panasonic RS-170 (Model WV-1500).

The video camera 118 is operatively connected to an analog-to-digital converter 120 by a cable. This serves to convert the preferred analog-to-digital converter 120 is an Electrohome NTSC video decoder, Model 38-80010-1 manufactured by Electrohome Electronics of Kitchner, Ontario. The analog-to-digital converter is in turn connected to a frame grabber board internally mounted in the data processing apparatus 106.

Data processing apparatus 106 preferably includes an IBM PCAT computer including a central processing unit 122 and keyboard 124, supplied as a unit from IBM of Boca Raton, Fla. The central processing unit 122 hereof is configured to include a 360 kilobyte floppy disk drive, an internal 30 megabyte hard drive, an Intel 80287 arithmetic co-processor chip, and additionally includes a DT2858 arithmetic co-processor board and a DT2851 frame grabber board, both from Data Translation Inc. of Marlboro, Mass.. The frame grabber board is an image memory device which stores an entire image and is conventionally called a frame buffer. Data processing apparatus additionally includes an external hard drive 126 with 85 megabyte capacity supplied by CMS of Tustin, Calif. which is connected as shown in the drawing to central processing unit 122. Data output apparatus 108 includes a video monitor 128, which is preferably an Electrohome 1311 (Model 38-DO5IMA-UP) from Electrohome Electronics of Kitchner, Ontario. The monitor 128 is connected to the DT2581 frame grabber board internally mounted in the central processing unit 122. The analog-to-digital converter 120 is connected to the video camera 118, the monitor 128 and the DT2851 output hookups by suitable electronic cable. The analog-to-digital 120 converter transforms a signal received from the video camera 118 into a pixel array in the image memory and conversely converts the pixel array into spatially organized image intensities on the video monitor 128.

The central processing unit 122 is also supplied with commercially available software for performing the method of the present invention. This software includes DT-IRIS available from Data Translation, Inc. as well as a tutorial for using the DT2851 frame grabber board entitled IRIStutor available from the same source. The software written for the method hereof is written in FORTRAN 77 and compiled with Microsoft Fortran V4.0 from Microsoft Corp. of Bellevue, Wash. In performing the various statistical calculations, the program utilizes a statistical program developed in conjunction with the present invention.

It is to be understood that the kernels are placed on the light table 102 and suitably illuminated so that the microscope and video camera may be located for acquiring the images of each kernel and its corresponding germ. As will be seen from the following explanation of the computer processing steps, the kernels need not be completely separated to present a clear surrounding area for identification, but the kernels are preferably arranged on the light table in a single layer to minimize the time associated with acquiring the requisite number of images to present a statistically significant sampling.

Figure 2:
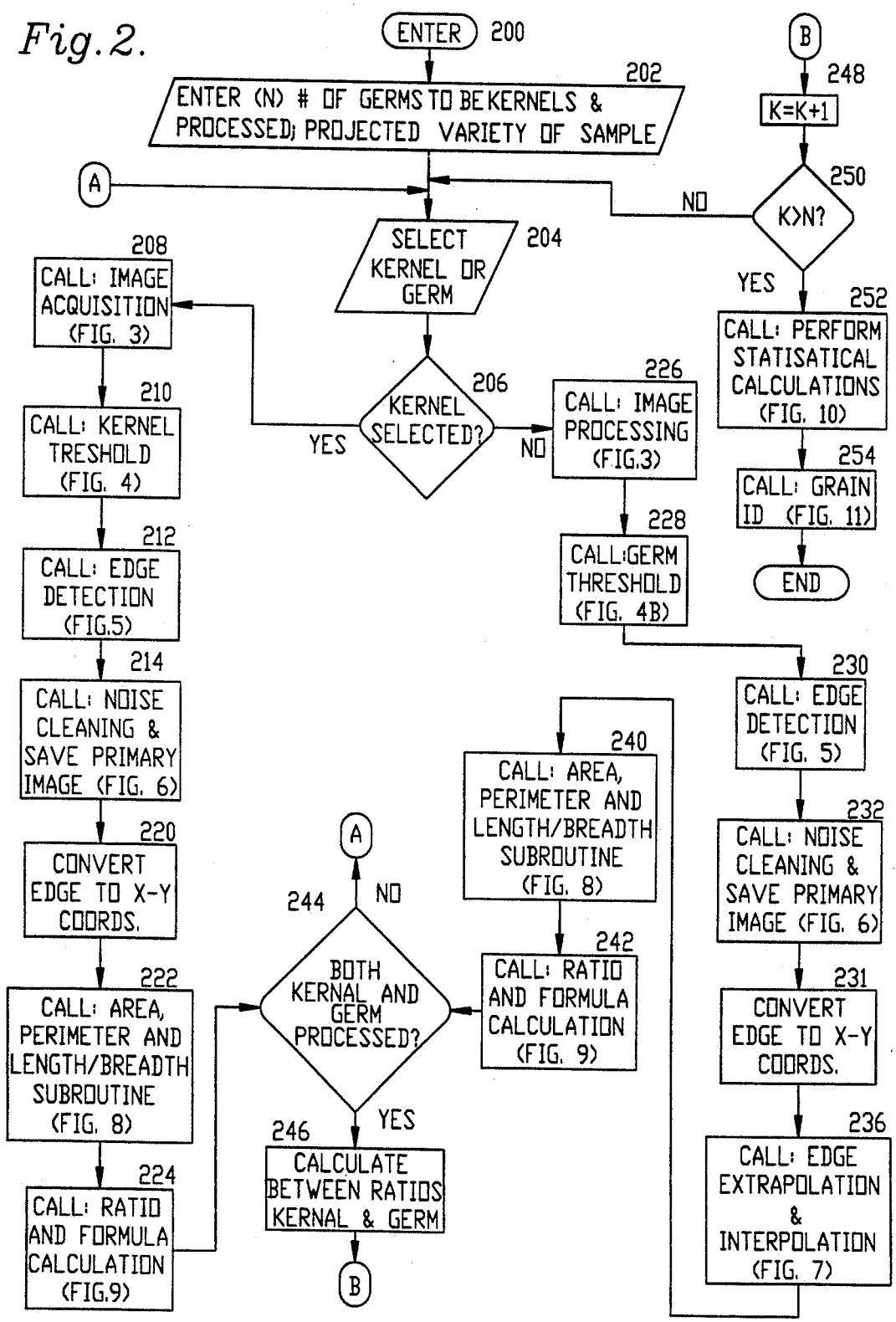
FIG. 2 is a computer program flowchart of the processing steps in accordance with the present invention.

Referring now to FIG. 2, the steps for operating the program hereof for identifying the grain samples are broadly designated by the numeral 200. In step 202, the operator enters on keyboard 124 the number of kernels to be processed and the anticipated or projected variety of the sample. Because each kernel contains a germ therewithin, the number of kernels and germs to be processed is the same. If the variety of the sample is unknown, the operator's entry reflects this fact and the program proceeds to step 204.

The program hereof is designed to treat the kernel image and germ image acquisitions as separate entities. The program prompts the operator whether the acquired image is to be a kernel or germ. In step 204, the operator selects whether a kernel or germ image is to be initially processed. The computer tests whether a kernel has been selected in step 206. If a kernel is selected, the program 200 proceeds to steps 208 through 224, while if a germ is selected, the program proceeds to steps 226 through 244.

An image for a kernel or germ is acquired by averaging three frames received from the video camera in analog format and processed through the analog converter into digital format. This technique serves to minimize or eliminate extraneous signal noise. The resulting full frame is convolved via a 3×3 lowpass filter. The filtering operation is performed by calling a DT-IRIS subroutine (IS_FILTER). The mask consists of 1's for multiplication coefficients and a divisor of 9. Because the filtering is performed on a gray image, blurring of the image is kept to a minimum.

When the image is acquired it is divided into rows and columns, and a box is drawn one row and one column out from the portion of the image that is to be saved. This technique is done to make sure that the image to be acquired exists within the boundary specifications of the "window" (IS_SET_ACTIVE REGION subroutine (ISSETR) of DT-IRIS). The IS-SETR subroutine defines the active region portion of the frame which is to be saved using the specified origin (starting row and column) and ultimate size of the image. The advantage of this subroutine is that it allows the operator to save only the important region or feature of interest within the acquired frame. In turn, the resulting requirement for the frame storage is decreased, as well as the processing time. Separate window sizes are set for the kernel (390×256) and the germ (255×256) images. Active regions are set liberally because the specimens are typically manually placed under the microscope 116. As a result, the margin of error for specimen placement is rather small.

In step 208, the program 200 calls the image acquisition program shown in FIG. 3 to acquire the image for the kernel and input that image to the central processing unit 122. The image is digitized into columns and rows of pixels. In step 210, the program calls the kernel threshold subroutine shown in FIG. 4A to identify the image of the kernel by setting a brightness threshold. The threshold levels serve to discriminate between the pixels having a brightness exceeding the threshold level corresponding to the surrounding illuminated area and the pixels whose brightness falls below the threshold level corresponding to the kernel. A binary matrix with values of 0 or −1 is created with each pixel being assigned a value corresponding to their brightness value relative to the threshold.

Figure 5:
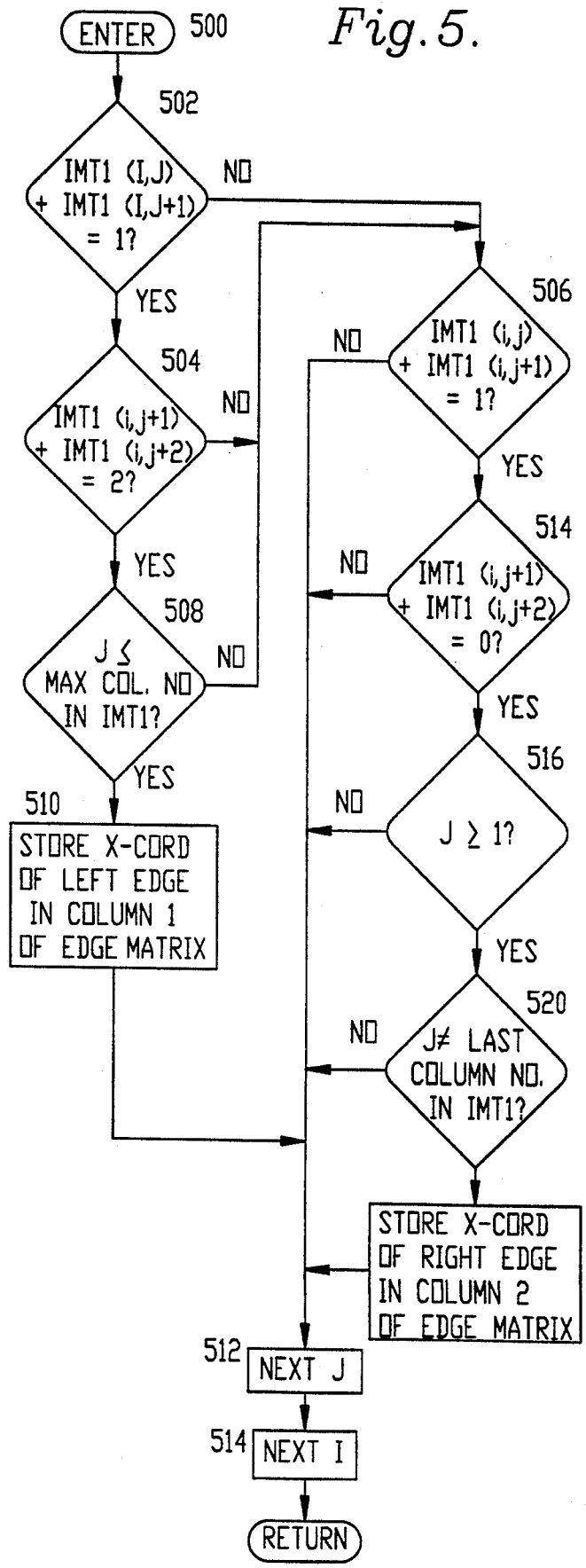
FIG. 5 is a computer program flowchart of the edge detection subroutine of the present invention.

In step 212, the program calls the edge detection subroutine shown in FIG. 5 which, having determined which pixels correspond to the kernel, now determine those pixels which represent the edge or perimeter of the kernel and stores the values in a matrix having the name EDGE. By determining which pixels correspond to the edge, a number of calculations can be performed to identify the size characteristics of the kernel.

Figure 6:
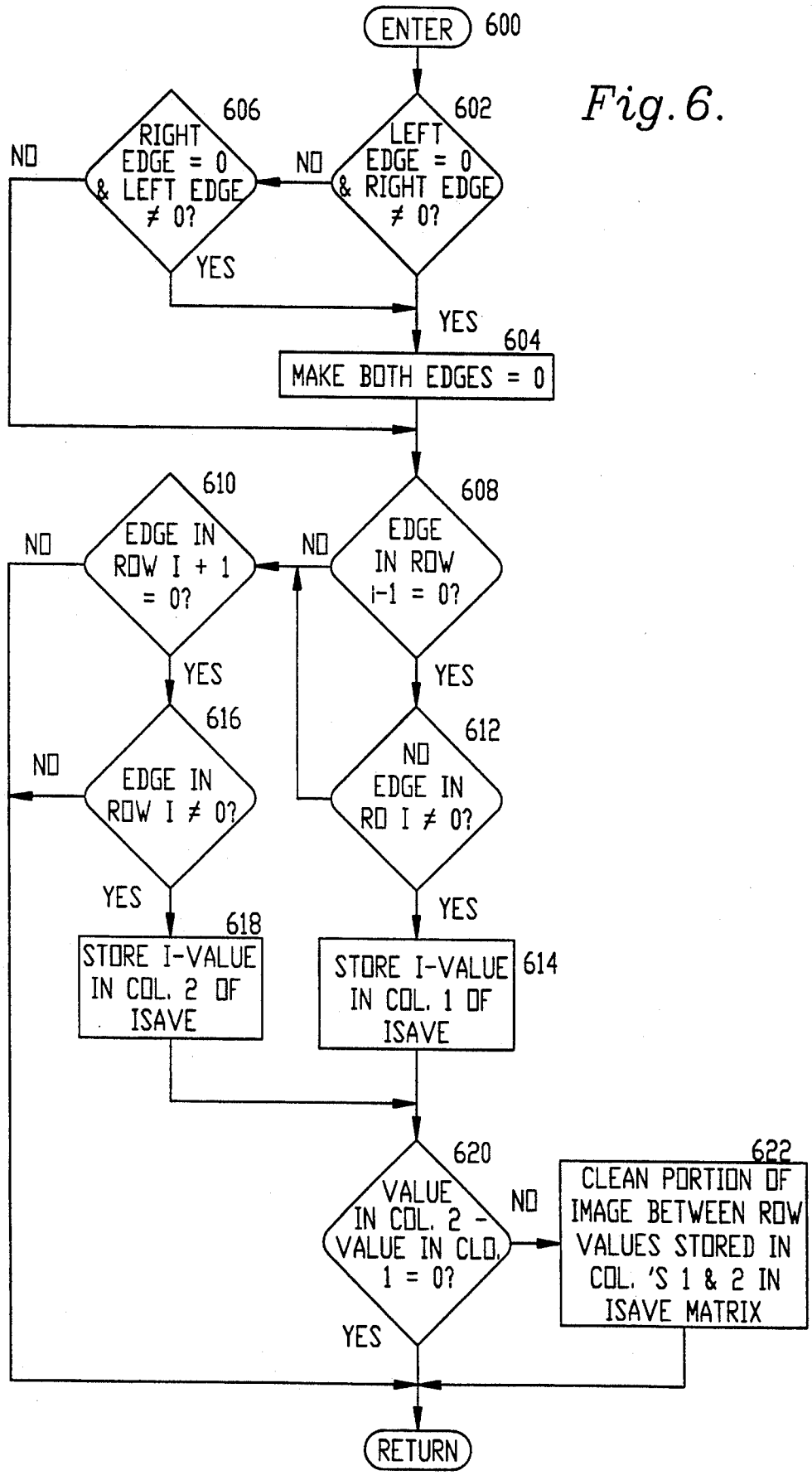
FIG. 6 is a computer program flowchart of the noise cleaning subroutine for the germ in accordance with the present invention.

In step 214, the program calls the noise cleaning subroutine shown in FIG. 6 which ascertains whether the image of any extraneous material has been acquired and deletes any such images from the stored image to be processed. Similarly, the save primary image subroutine is also called in step 214 and further illustrated in FIG. 6. The save primary image subroutine serves to eliminate the image of edge points not associated with the primary image and save the image of only the principal kernel image.

Figure 9:
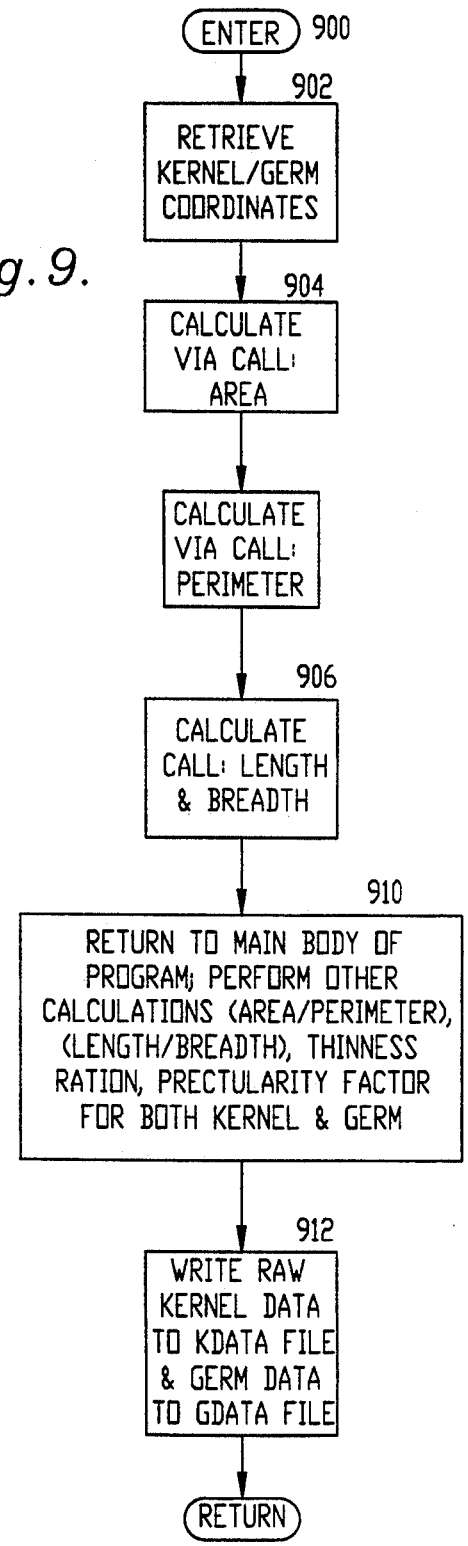
FIG. 9 is a computer program flowchart of the ratio and formula calculations and subroutines in accordance with the present invention.
Figure 8:
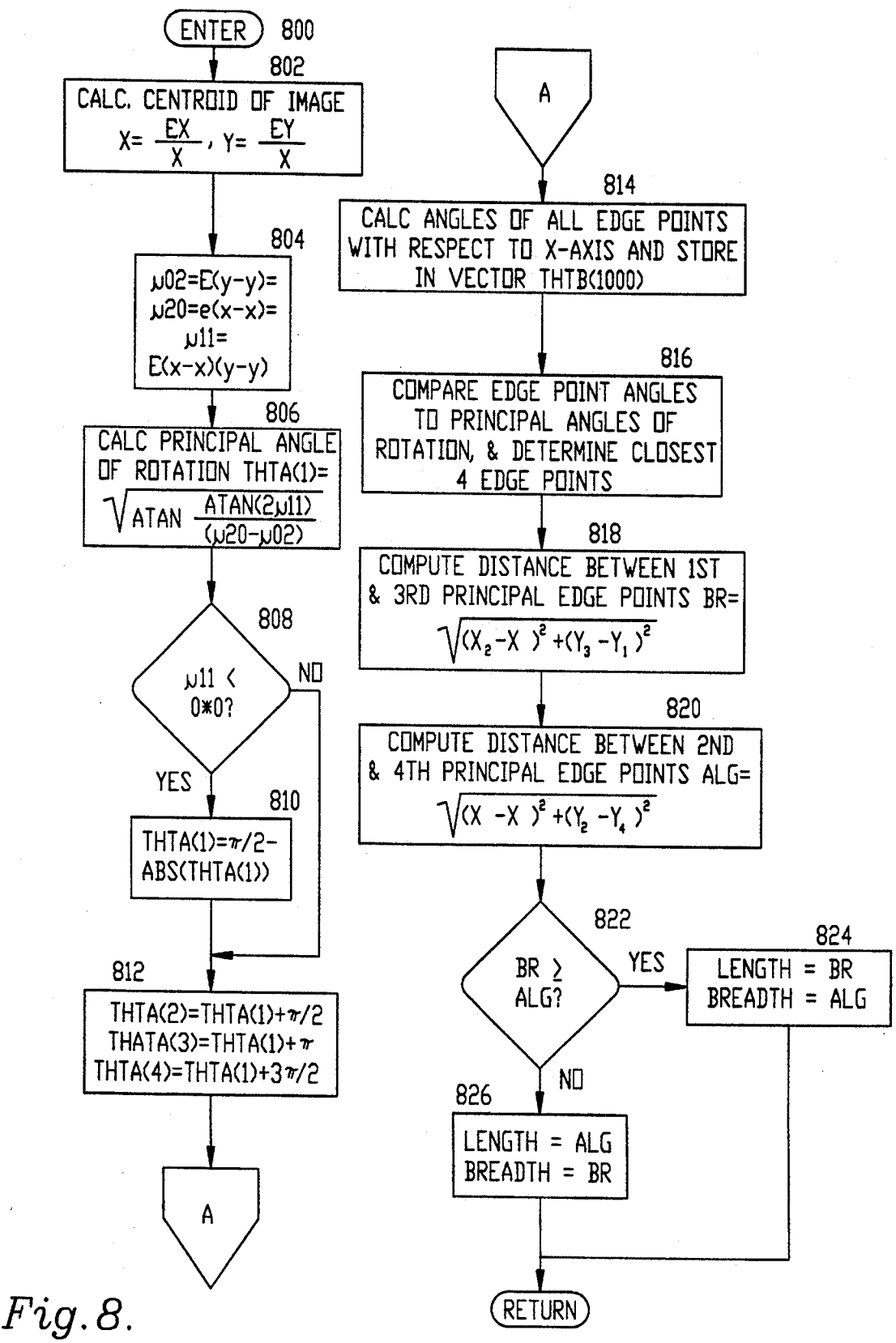
FIG. 8 is a computer program flowchart of the area and length/breadth calculation subroutine in accordance with the present invention.

In step 220, the program converts the digital image from rows and columns to X-Y coordinates and stores the resulting values in a matrix called COORD. This enables the computer to determine the major and minor axes of the kernel. In step 222, the program calculates the area and perimeter of the kernel and in step 224 the program determines the length and breadth as well as the centroid of the kernel, as shown in FIG. 8. In step 224 the ratio and formula calculations are found in the subroutine as shown in FIG. 9 to calculate such identifying criteria as formfactor or thinness ratio and a rectularity factor. Before proceeding to additional calculations, the program returns to step 226 for processing the germ image.

In step 226, the program reads the images stored from the acquisition program shown in FIG. 3, which performs substantially the same steps on the germ as for the kernel. In step 228, the program calls the germ thresholding subroutine shown in FIG. 4B. The germ thresholding subroutine is that illumination to define the germ within the kernel is somewhat more difficult than determining the difference between the kernel and the surrounding backlit area. The pixels corresponding to the edge of the germ are determined and stored in the EDGE matrix.

In step 230, the program calls the edge detection subroutine to determine the pixels corresponding to the edge of the germ. This subroutine is shown in FIG. 5 and is the same in operation as described in step 212 above. Step 232 involves the noise cleaning subroutine and save primary image subroutine (FIG. 6) whose function was broadly described above with reference to step 214.

Step 234 converts the row and column values of the EDGE matrix to X-Y coordinates stored in a matrix called COORD as described broadly for the kernel in step 220.

Figure 7:
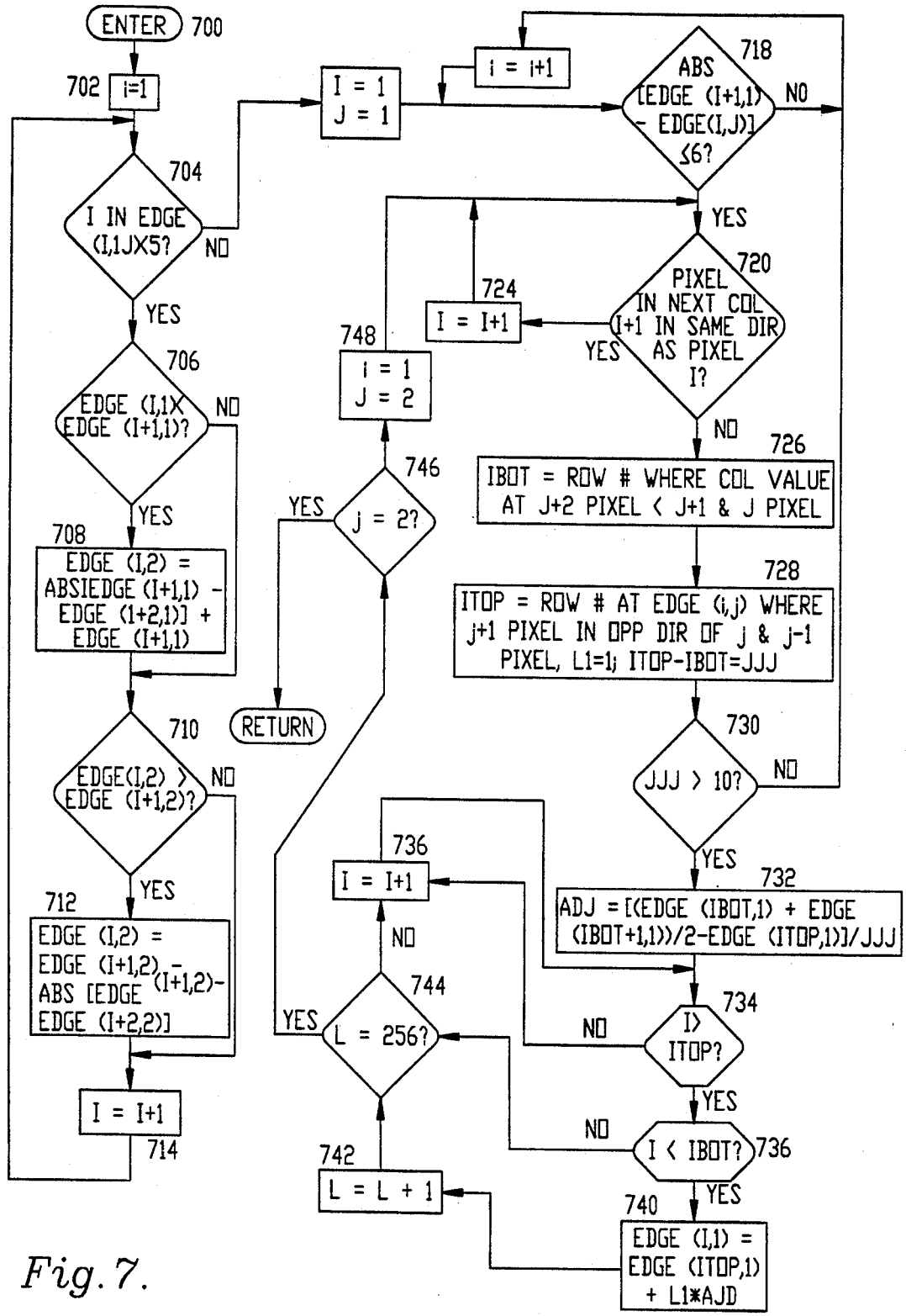
FIG. 7 is a computer program flowchart of the edge extrapolation, interpolation and cleaning check-point subroutine for processing the kernel images in accordance with the present invention.

Step 236 calls the edge extrapolation and interpolation subroutine as shown in FIG. 7. The edge extrapolation processing is unique to the germ images because of the variation in germ shape and interior inclusions. Though the "true" edge is determined, it may be discontinuous and the edge pixels must be connected for accurate measurements to be made. Thus, during edge extrapolation, the subroutine searches for any discontinuities in the germ and attempts to resolve the germ image into a "standard"image.

Step 236 also includes the edge interpolation processing shown in the subroutine illustrated in FIG. 7. Step 240 is shown in FIG. 8 and involves the measurement of the germ according to its resolved X-Y coordinates to determine the length, breadth, area and perimeter of the germ. In step 242, the program calls the ratio and formula calculation subroutine shown in FIG. 9 to determine the pertinent ratios for the germ such as the area to perimeter ratio, the length to breadth ratio, and the formfactor and rectularity factor of the germ. Formfactor is an indication of the shape of an object. To calculate formfactor of an object, the following equation may be used: Form-factor$=4*pi*area/perimeter^2$.

Step 244 tests to see of both the kernel image and the germ image for a particular grain specimen have been processed. If the answer is "yes", the program proceeds to step 246, and if the answer is "no" the program returns to step 204.

In step 246, the program calculates various ratios dealing with the measurements taken and calculated for the germ and the kernel. For example, the calculations include the ratios of the kernel area to the germ area, the kernel perimeter to the germ perimeter, the kernel length to the germ length, and the kernel breadth to the germ breadth. The program proceeds to step 248 where the number of the kernel being processed is incremented by one. In step 250, the program tests to see if the new kernel number K exceeds the number N of kernels to be processed. If the answer is no, the program returns to step 204.

Figures 10, 11:
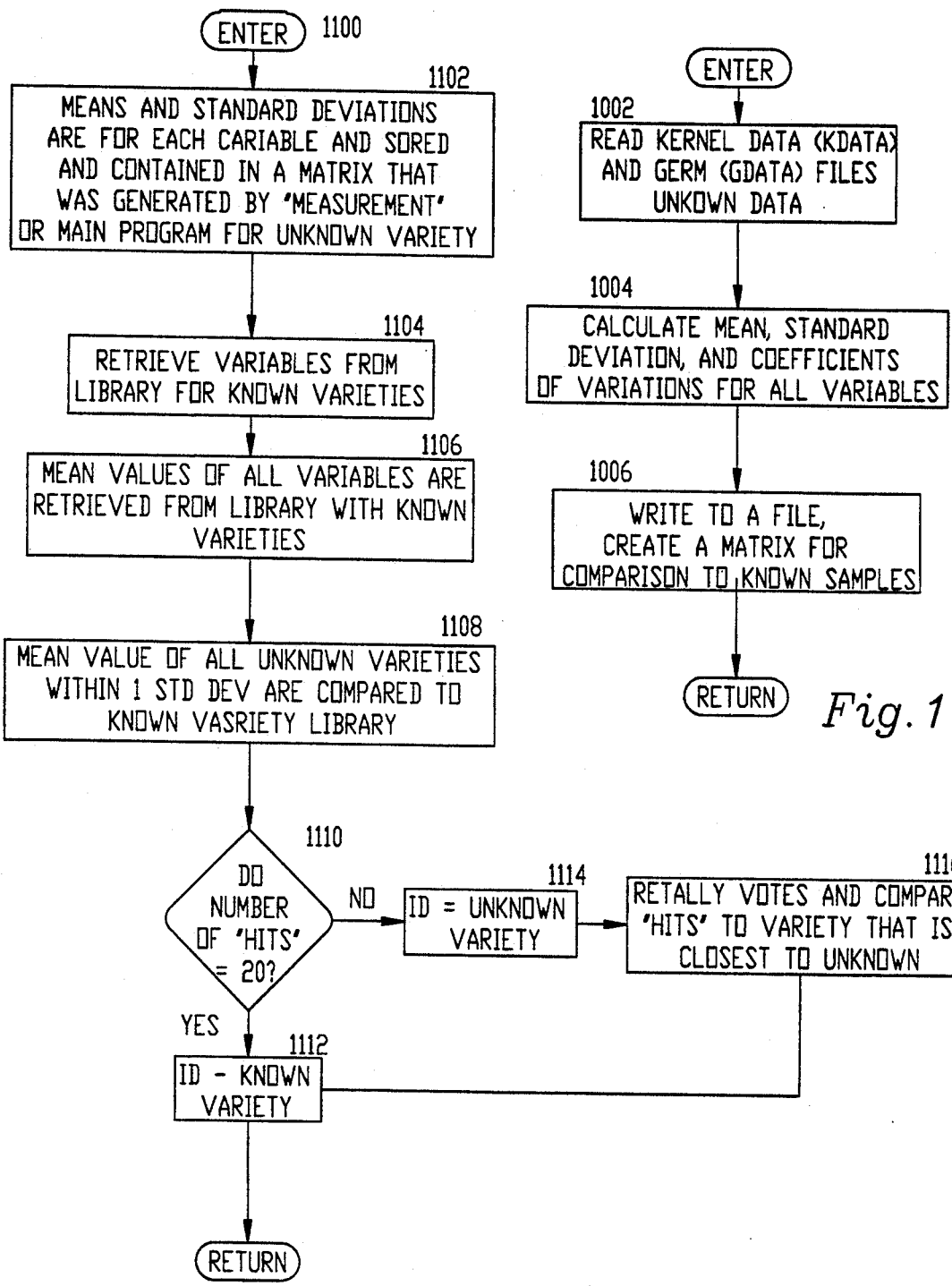
FIG. 10 is a computer program flowchart of the conversion of raw image data to statistically summarized data in accordance with the present invention.
FIG. 11 is a computer program flowchart of the grain identification program of the present invention.

If the answer is yes, the program proceeds to step 252 where the program calls the grain identification data as shown in FIG. 10. This program performs the statistical calculations for the sample. The grain ID program is then called in step 254 and determines if the sample has a sufficient number of discriminators according to the standard deviation selected to permit identification of the sample as a particular grain cultivar or variety. For example, 20 out of 20 discriminators might be required to fall within plus or minus one standard deviation of a known sample stored in the computer memory in order to permit positive identification. The identification of the sample is preferably based on a 100 kernel sample size which differs greatly from an identification on a kernel by kernel basis. It should be noted that as the number of kernels in the sample is increased, the level of confidence of a proper identification is similarly increased.

In addition, in the event mixed samples are examined, the method hereof may separate the mixed sample into pure samples or indicate the percentage of each cultivar in the mixed sample. The algorithm utilizes a transformation of a 14-bin histogram to separate a mixed sample from a pure sample of a single cultivar. The important variable in this separation is the ratio of kernel breadth to germ breadth.

The image acquisition program is shown in greater detail in FIG. 3 and is broadly represented by the reference character 300. The image acquisition subroutine 300 begins with step 302 where the computer receives the image from the camera. In step 304, three frames of the image are averaged to yield an average pixel value which minimizes noise received with the image. In step 306, the image received is further filtered by the DT-IRIS subroutine IS_FILTER. The filtering is performed on a gray image, thus minimizing blurring. At step 308, the program outlines the active region of the image. The program determines the active portion of the saved image by using the ISSETR subroutine of the DT-IRIS program. The active region is the portion of the frame having an image rather than mere background and is saved using the starting row and column and ultimate size of the image. The program places an outline around the image, preferably creating a box one column and one row out in the image matrix from the saved image. This step is performed to make sure an image exists within the boundary specification of the "window" established by the ISSETR subroutine of DT-IRIS. In step 310 the program displays the image on the monitor. At step 312, the program again outlines the active region of the image and at step 314 defines the active region of the subroutine. At step 316, the program asks the operator whether he or she desires to save the image. If the input from the keyboard 124 is "no", the program returns to step 302 to reacquire an image. If the input is "yes", the program exits to the main program.

FIG. 4A represents the kernel thresholding subroutine and is broadly designated by the reference character 400. In step 402, the program reads the stored brightness levels for the kernel pixels in the saved image and places them in the vector IMT1. Next, in step 404, the program tests to see if the value of IMT1 is greater than or equal to 0 but less than or equal to 100. If the answer is "yes", the program proceeds to step 406 and sets the value of IMT1 to −1, thus constituting a background pixel. On the other hand, if the answer is "no", the program proceeds to step 408 and sets the value of IMT1 equal to 0, thus constituting an image pixel.

Figure 4B:
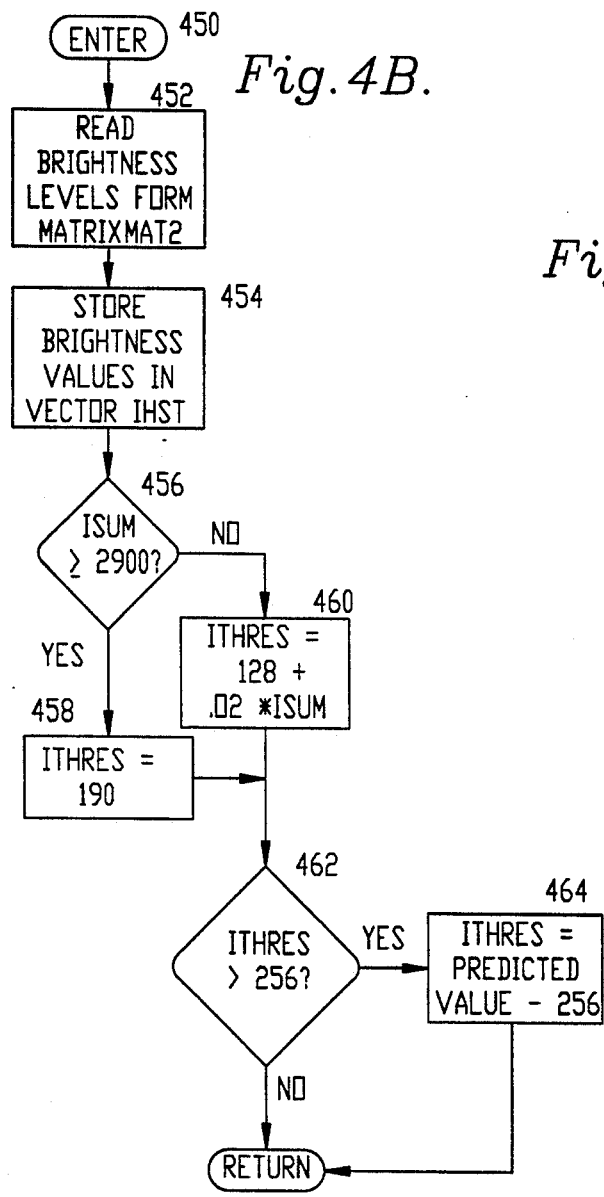
FIG. 4B is a computer program flowchart of the germ thresholding subroutine of the present invention.

FIG. 4B illustrates the germ threshold and subroutine and is broadly designated by the reference character 450. In step 452, the program reads the brightness levels for the pixels for the germ image from the matrix MAT2. Next, in step 454, those images are stored in the vector IHST. Step 456 tests to see whether the value ISUM which is the summation value of the tallied grey levels for the last 50 rows of the tally vector (256) is greater than or equal to 2900. This is an arbitrary value chosen as the cutoff summation row for each acquired image. ISUM is fairly indicative of how well the germ is lit in the acquired image.

If the value of ISUM is greater than or equal to 2900, the value of ITHRES, the threshold value for a particular lamp distance, was set as equal to 190 in step 458. If the value of ISUM was not greater than or equal to 2900 in step 456, the program proceeds to step 460 where the value of ITHRES is set as equal to 128 plus 0.02 multiplied times the value of ISUM. The program next proceeds to step 462 to test whether the value of ITHRES is greater than 256. If the answer is "yes" the program proceeds to step 464 where the value of ITHRES is set as equal to the predicted value for ITHRES minus 256 and then the subroutine returns to the main program. If the value of ITHRES does not exceed 256, the value ITHRES retains its previously calculated value as determined by either step 458 or 460, and returns to the main program.

The program must determine the edge of the image and this is done in the edge detection subroutine broadly designated by the reference character 500 in FIG. 5. The edge detection subroutine as shown in the source code of a preferred embodiment of the invention, appendix I, by the subroutine name EDETN. Each pixel is arranged in 256 columns (j) and 256 rows (i). The initial values of i and j are each one so that the subroutine begins with the first column and the first row. The edge detection subroutine begins with step 502. In step 502, the program tests to see if the absolute value of the matrix IMT1 at row I, column J plus the value of IMT1 at row I, column J plus 1 is equal to 1. If the answer is "yes", the pixel identified at IMT1 (i,j) is a possible edge point and the program proceeds to step 504. If the answer is "no", the program proceeds to step 506 and once again tests to see if the value of IMT1 at row I, column J is equal to 1.

At step 504, the program tests to see if the value of IMT1 row I, column J plus 1 plus the value of IMT1 at row I, column J plus 2 is equal to 2. If the answer is "no", the program proceeds to step 506. If the answer is "yes", the program proceeds to step 508 where the program tests to see if the value of J representing the column is less than the maximum column number in IMT1. If the answer is "yes", the program proceeds to step 510 where the program stores the X coordinate of the left edge of column 1 of the edge matrix. The program then proceeds to step 512 where a new column value is assigned to the variable J.

If the answers to any of the tests performed in steps 502, 504 or 508 are negative, the program proceeds to step 506 and performs the test indicated therein to see if the value IMT1 at row I, column J plus the value at row I, column J plus 1 is equal to 1. If the answer is "no", the program proceeds to step 512 and tests the value of IMT1 at the next column. If however, the answer to the test performed at step 506 is "yes", the program proceeds to step 514 and tests to see if the sum of IMT1 at row I, column J plus 1 and IMT1 at row I, column J plus 2 equals 0. If the answer is "yes", the program proceeds to step 516. At step 516, the program tests to see whether the value of J is greater than or equal to 1. If the answer is "yes", the program proceeds to step 518 which tests to see if the value of J, corresponding to the column number being tested is not equal to the last column number in IMT1. If J is not equal to the last column number, then the program stores the X coordinate of the right edge in column 2 of the edge matrix at step 520 and proceeds to step 512 to test the next column. If the answers to any of the tests performed at steps 506, 514, 516 or 518 is negative, the program proceeds to step 512 and increments the value of J to the next column. Once all the columns for a particular row I are tested, the value of I is incremented at step 514 until all columns in all rows have been tested and then the program returns to the main program.

The EDGE matrix may contain entries which correspond to stray pixels, imperfections, lens spots or other noise which are desirably eliminated in order to minimize processing time and improve efficiency. FIG. 6 represents the noise cleaning subroutine and is broadly designated by the reference character 600 and referenced in Appendix I, the flowchart appended hereto, as MRCLEAN.

Step 602 initially tests to see whether a row of the EDGE matrix contains both a zero value and a number which is greater than zero (L value) in the opposing column. If the answer is "yes", the program proceeds to step 604 and sets the left and right edges corresponding to that row in the EDGE matrix equal to zero. If the answer to the test performed at step 602 is "no", the program proceeds to step 606 and tests to see whether, for that row in the EDGE matrix, the right edge is equal to zero and the left edge is not equal to zero. If the answer is "no", then the row contains two "L" values and a possible edge of the image is determined for further testing. If the answer to the test performed in step 606 is "yes", the program proceeds to step 604 and sets both edges equal to zero.

In step 608, the program tests to see whether the value for the edge in row I minus 1 (the previous row) is equal to zero. If the answer is "no", the program proceeds to step 610 and tests to see whether the value for the I plus 1 row (the succeeding row) is equal to zero. If the answer to the test performed in step 608 is "yes", the program proceeds to step 612 to test whether or not the value of EDGE in row I is not equal to zero. If the answer is "no", the program proceeds to step 610, but if the answer to the test performed in step 612 is "yes", then the value of I for that particular row is stored in column 1 of ISAVE as an "in" pixel corresponding to the left side of the image in step 614.

If the answer to the test performed in step 610 is "yes", then the program proceeds to step 616. In step 616, the program tests to see whether the value for EDGE at row I is not equal to zero. If the answer is "yes", the program proceeds to step 618 and stores the value of I for that row in column 2 of the ISAVE matrix. In the event that the answer to either test performed in steps 610 or 616 is "no", the program proceeds to test the next row until all rows are tested and then returns to the main program.

After the steps 614 and 618 are performed, the program proceeds to step 620 where the program tests to check if the value in column 2 of the ISAVE matrix minus the value in column 1 of the ISAVE matrix equals zero, indicating that the same pixel constitutes both an in and an out point. If the answer is "yes", the program proceeds to test the next row until all rows are tested and then returns to the main program. If the answer is "no", the program proceeds to step 622 which cleans, i.e. sets the value in EDGE to zero, the portion of the image between the row value stored in columns 1 and 2 of the ISAVE matrix. The program then processes the next row until all rows are tested and then returns to the main program.

FIG. 7 illustrates the edge interpolation subroutine for smoothing the image. The edge interpolation procedure examines the left side of the image, and thus the first column in the EDGE matrix, and then performs the same function for the right side of the image which is performed on the second column of the EDGE matrix. The edge interpolation subroutine which is broadly designated by the numeral 900 also includes an upper image method and utilization algorithm which addresses a line extension problem from the image at the upper end thereof. This subroutine is part of the SMOOTH subroutine set forth in the source code appearing in appendix I.

The edge interpolation subroutine begins with step 702 which initiates the upper image utilization algorithm. The counter for the column and row in the EDGE matrix begins at row 1, column 1. At step 704, the program checks to see if the EDGE matrix value of i is less than 5, and therefore in the first 4 rows. If the answer is "no", the subroutine proceeds to the edge interpolation portion beginning at step 716. If the answer is "yes", the program proceeds to step 706 to test for whether the LVALUE (left edge point) in row i, column 1 of the EDGE matrix is of a lesser value than the LVALUE of row i+1, column 1. If the answer is "no", the program skips to step 710, but if the answer is "yes", the LVALUE of EDGE (i, 1) is set equal to the absolute value of the LVALUES of EDGE (i+1, 1) minus EDGE (i+2, 1), plus EDGE (i+1, 1).

In step 710, the program tests the LVALUE of row i, column 2 of the EDGE matrix to see if it is greater than the LVALUE of row i+1, column 2. If the answer is "yes", the program proceeds to step 712 but if the answer is "no", the program skips to step 714. Because the left side of the kernel or germ should curve outwardly on the right side (LVALUE increasing) for the first five rows, an error has been picked up in the image which must be corrected. At step 712, the programs sets a new corrected LVALUE in the EDGE matrix for row i, column 2 as the LVALUE of EDGE (i+1, 2) plus the absolute value of the difference between the LVALUEs of EDGE (i+1, 2) and EDGE (i+2, 2). This completes the upper image utilization algorithm for that row in the EDGE matrix, and the value of i is incremented by one to test the next row at step 714. The process is repeated until the value of i reaches 5.

Step 716 begins the edge interpolation portion of the subroutine which serves to resolve any deep inclusions which would otherwise give the kernel or germ a "pac-man" shape. Such a shape is defined by the program as a series of pixels which make a stepwise entrance into the interior of the image beginning from an in or out edge boundary column and then turning back sharply in the direction of the actual or "normal" in or out edge boundary. Step 716 begins by setting the row counter i to 1. In step 718, the program detects a stepwise entrance into the image by taking the difference between two successive column LVALUEs stored in the EDGE (i, j) matrix. If the resulting value is less than or equal to 6, the subroutine will proceed to the LVALUE for that column in the next row to see if that pixel is moving in the opposite direction to that of its predecessor. If a pixel is moving in the opposite direction to that of its predecessor, the difference between the two LVALUEs should be negative. The choice of 6 as a value was liberally chosen because a stray row of pixels was sometimes encountered.

Step 718 thus tests the absolute value of the difference between the LVALUEs at EDGE (i+1, 1) and EDGE (i, 1) to see if it is less than or equal to 6. If the answer is "yes", the program proceeds to step 720. If the answer to the query posed at step 718 is "no", the program proceeds to step 722 which adds 1 to the value of i.

Step 720 checks to see if the pixel at EDGE (i+1, 1) is moving in the same direction as the pixel at EDGE (i, 1). If the answer is "yes", 1 is added to the value of i in step 724 the program returns to step 718 to test the pixel in the next row for column 1. If the answer is "no", the program proceeds to step 726 which sets the value of the variable IBOT equal to the row number where the LVALUE at EDGE (i+2, 1) is less than the LVALUE of EDGE (i+1, 1). In step 728, the program sets the value of the variable ITOP as equal to the row number i in EDGE (i, 1) where the LVALUE of the (i+1) pixel moves in the opposite direction of the i and (i−1) pixel. Step 728 also establishes an integer counter value L1 which is successively generated each time within a loop and is initially set to a value of 1. Step 728 also calculates the value of the variable JJJ which is the difference between IBOT and ITOP.

Step 730 then tests to see if the value of JJJ is greater than 10. If the answer is "yes", interpolation will be performed and the program proceeds to step 732. If the answer is "no", no interpolation will be performed and the value of i will increment by 1 to test the next pixel at step 722. Interpolation is performed at step 732 by setting the variable AJD equal to the LVALUE computed as follows:

AJD=(([EDGE (IBOT, 1)+EDGE (IBOT+1, 1)]×1.0÷2.0)−EDGE (ITOP, 1)×1.0)÷(JJJ×1.0)

The program then proceeds to step 734 which checks to see if the value of i is greater than ITOP. If the answer is "no", the program increments the value of i by 1 at step 736. If the answer is "yes", the program proceeds to step 738 which tests to see if the value of i is less than IBOT. In the answer is "no", the program proceeds to step 744.

If the answer to the query posed in step 738 is "yes", the LVALUE of the EDGE matrix at EDGE (i, 1) is set equal to EDGE (ITOP, 1)+(L1×the value of AJD) in step 740. The program then proceeds to step 742 which increments the value of L by 1 and then to step 744 which tests to see if the value of the row counter i is equal to 256. If the answer is "yes", the program proceeds to step 746. If the answer is "no", the program proceeds to step 736 which adds 1 to the value of i.

The procedure for processing the second column is accomplished by steps 746 and 748. Step 746 tests to see if the column counter j is equal to 2 (the right-hand column). If the answer is "yes", then all rows have been processed and the subroutine returns to the main program. If the answer is "no", the program proceeds to step 748 which resets the row counter i to 1 and the column counter j to 2. The program then proceeds from step 742 to 718.

FIG. 8 illustrates the subroutine for resolving the image into x and y cartesian coordinates and the length and breadth of the image. This subroutine is broadly designated by the reference character 800. The subroutine begins at step 802 wherein the centroid of the image is defined as being the average x and y coordinates. Thus, the average x coordinate is determined by taking the sum of all the x values and dividing by the number of x edge points in the EDGE matrix, and the average y coordinate is determined by taking the sum of all y values and dividing by the number of y edge points in the EDGE matrix.

In step 804, the program determines the central moments $\mu 02$ corresponding to the y axis, $\mu 20$ corresponding to the x axis and $\mu 11$ which is the combined central moment for the x and y axis. The computer program hereof performs that calculation by initially setting the value of x to 0.0 and y is equal to zero, then recomputing the value of x as equal to x plus EDJ(I1,1) and y as equal to Y plus EDJ(I1,2), where I1 is equal to 1,K (where K is the number of edge points). This is performed in a DO loop for each of the edge points. The program then continues to determine the value of XB as being equal to X divided by K times 1.0 and Y as being equal to Y divided by K times 1.0. $\mu 20$, $\mu 02$ and $\mu 11$ are initially set to 0. Moments of inertia are then calculated as:

DO 210 I2=1,K
X1=EDJ(I2,1)−XB
Y1=EDJ(I2,2)−YB
$\mu 02 = \mu 02 +$(absolute value(EDJ(I2,2)−YB))$^2$
$\mu 20 = \mu 20 +$(absolute value(EDJ(I2,1)−XB))$^2$
$\mu 11 = \mu 11 + (X1 \times Y1)$ These central moments are then used in calculating the principal angle of rotation THETA(1) in step 806. There, the principal angle of rotation THETA(1) is computed as follows:

$$\Theta(1) = \sqrt{\arctangent(2\mu 11 \div (\mu 20 - \mu 02))}$$

Next, in step 808, the program tests to see if the value of $\mu 11$ is less than 0.0. If the answer is "yes", the program proceeds to step 810 where the value of THETA(1) is recalculated as being equal to $\pi/2$ minus the absolute value of THETA(1) as computed in step 806. If the answer to the test performed in step 808 is negative, the program skips step 810 and proceeds to step 812 to determine the remaining angles of the principal axes by adding multiples of $\pi/2$ to obtain THETA(2), THETA(3) and THETA(4) as shown in step 812. The program then proceeds to step 814 wherein it calculates the angles of all the edge points with respect to the x axis and stores these calculations in a vector THETA B of 1000 registers.

The program then proceeds to step 816 and compares the edge point angles to the principal angles of rotation and determines the four edge points which are closest thereto. These become the four principal edge points. Next, in step 818, the program computes the distance between the first and third principal edge points to determine the breadth of the image, this being determined by the calculation:

$$BR = \sqrt{(X_3 - X_1)^2 + (Y_3 - Y_1)^2}$$

Next, in step 820, the program computes the distance between the second and fourth principal edge points to determine the length of the image, ALG, this being determined by the calculation:

$$ALG = \sqrt{(X_2 - X_4)^2 + (Y_2 - Y_4)^2}$$

In step 822, the program next tests to see whether breadth is greater than the length as determined by the foregoing calculations performed in steps 818 and 820. If the answer is "yes", the values are reversed. That is to say, the program proceeds to step 824 and reassigns the previously computed value of BR as LENGTH, and the value of ALG as BREADTH. If the answer to the test performed in step 824 is "no", the program proceeds to step 826 and sets LENGTH equal to ALG and BREADTH equal to BR for that image. After completing either step 824 or 826, the subroutine returns to the main program.

FIG. 9 illustrates the flow diagram for determining the formula calculations performed in accordance with the invention hereof. The program used in performing the calculations is broadly designated by the reference character 900. This program is useful to yield the values for the grain identifying discriminators which are used to identify the particular cultivar. The image having been resolved into x and y co-ordinates in FIG. 8, the ratio and formula calculation subroutine ascertains the values for the particular discriminators for that image. The ratio and formula calculation program calculates the values for the following discriminators for either the kernel image or the germ image and their corresponding variable names as used in the source code appended hereto as appendix I:

| DISCRIMINATOR | ABBREVIATION |
| --- | --- |
| Kernel Area | K AREA |
| Kernel Perimeter | K PERM |
| Kernel Length | K LENGTH |
| Kernel Breadth | K BREADTH |
| Kernel Area/Kernel Perimeter | KAP |
| Kernel Length/Kernel Breadth | KLB |
| Kernel Thinness Ratio | TRK |
| Rectularity Factor (Kernel) | RECTK |
| Germ Area | G AREA |
| Germ Perimeter | G PERM |
| Germ Length | G LENGTH |
| Germ Breadth | G BREADTH |
| Germ Area/Germ Perimeter | GAP |
| Germ Length/Germ Breadth | GLB |
| Germ Thinness Ratio | TRG |
| Rectularity Factor (Germ) | RECTG |

The term "thinness ratio" as used herein is calculated as four times $\pi$ times the area divided by the perimeter. This calculation is performed using the respective values for the kernel or germ area and perimeter as appropriate. The term "rectularity factor" is defined as the area divided by the length times the breadth corresponding to the respective kernel or germ image being analyzed.

The ratio and formula calculation subroutine begins with step 902 which retrieves the x and y coordinates in the COORD matrix for the kernel or germ image to be processed. In step 904, the program calculates the area of the image (kernel or germ) by calling the area subroutine. This calculates the area, which is defined as the number of pixels within a defined boundary. The area calculation uses the COORD matrix and the following formula:

$$XX = [COORD (I+1, 1) + COORD (I, 1)]/2.0$$

$$YY = [COORD (I+1, 2) + COORD (I, 2)]$$

$$AREA = \Sigma XX + YY$$

The program next proceeds to step 906 wherein the program calls the perimeter subroutine for the respective kernel or germ. The perimeter involves a boundary-length calculation which sums the distances between a series of line segments connecting the boundary coordinates. To make the calculation indicative of a smooth function and to overcome falsely high readings due to edge jaggedness, the a mean value of three consecutive X and Y coordinates from the COORD matrix are taken. The total of these mean values for the entire boundary constitute the final perimeter value which is stored by the computer. For example, the X and Y values for row I of the COORD matrix would be calculated:

$$X1 = [COORD(I-1, 1) + COORD(I, 1) + COORD(I+1, 1)]/3.0$$

$$Y1 = [COORD(I-b\ 1, 2) + COORD(I, 2) + COORD(I+1, 2)]/3.0$$

$$Perimeter = \Sigma Xn + Yn$$

Next, in step 908, the program retrieves the value for the length and breadth of the image. At step 910, the subroutine returns to the main body of the program to perform additional calculations to determine the additional discriminators involving combinations of previously ascertained and calculated information. In step 910, the program calculates the ratio of the area to the perimeter, length to the breadth, the thinness ratio and rectularity factor for both the kernel and germ. Finally, in step 912, the raw data concerning the kernel is written to the file KDATA and the germ data is written to the file GDATA.

Referring now to FIG. 10, in order to identify the grain sample, the program must convert the raw data to statistically summarized data using the program STAT1.FOR. In order to accomplish this result, the program shown in FIG. 10 is utilized and broadly identified by the reference character 1000. In step 1002, the program reads the kernel data (KDATA) and germ data (GDATA) files for the unknown grain samples. The program then proceeds to step 1004 to calculate the mean, standard deviation and coefficients of variation for each discriminator used in identifying the unknown grain sample. Thus, the data from each kernel and germ is integrated into a composite, statistically resolved sample. The program then proceeds to step 1006 and writes the data calculated in step 1004 to a file, and creates a matrix for use in comparison of the data to known grain samples.

FIG. 11 illustrates the program for identifying the sample, which is shown in appendix I as the STATID.-FOR program. The program for identifying the sample using the previously statistically summarized data is broadly identified by the reference character 1100. The program begins by storing the mean and standard deviation for each variable by physically measuring the sample or by using the statistically summarized data in step 1102. In step 1104, the program retrieves the variables or discriminators for known grain varieties from internal memory, an internal disk, diskette, tape or other memory medium associated with the computer containing the library for the known varieties of the grain sample. In step 1106, the mean values of all discriminators are retrieved from the library for all known varieties. Then, in step 1108, the program compares the mean value of all the discriminators for the unknown sample which are within one standard deviation to the discriminators from the library corresponding to known samples, and tests to determine if there is sufficient correlation. In step 1110, the program tests to see if there are enough "hits", or corresponding discriminators common to a known variety and the unknown sample. If the answer is "yes", the program identifies the sample as the known variety in step 1112 and displays or writes out the cultivar of the sample. For example, each "hit" corresponding to a match between the mean of an unknown discriminator and the mean of the corresponding discriminator of the known sample plus or minus one standard deviation. Each "hit" can be stored in a vote tallying vector. If the number of votes exceeds a predetermined number, the sample is identified. It has been found that a total of 20 "hits" between a known and unknown sample will work well in identifying the cultivar of an unknown sample.

If there is insufficient correlation to identify the sample, then the program proceeds to step 1114 and displays or writes a message identifying the sample as an unknown variety. This can occur whenever the data in the library for known samples is incomplete and thus does not include the cultivar of the unknown, or when the sample is a mixed sample for which no positive identification can be made. The program may then proceed to step 1116 and retally the "votes" or discriminators and compare the discriminators of the unknown variety to the values from the library for the known varieties to determine the highest number of "nits" or closest correlation. The program will then proceed to step 1112 and identify the known variety with the greatest number of "hits" as the closest known variety. After the identification (or lack thereof) has been written and/or displayed on the monitor, the program exits.

Although preferred forms of the invention have been described above, it is to be recognized that such disclosure is by way of illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventors hereby state their intent to rely on the Doctrine of Equivalents to determine and assess the reasonably fair scope of their invention as pertains to any apparatus not materially departing from but outside the liberal scope of the invention as set out in the following claims.

We claim:

1. A method of identifying the cultivar of a grain sample having a kernel of grain with the kernel including a germ therein, said method comprising the steps of:

receiving sample image data representative of an image of a kernel of grain into a data processing device;

determining kernel edge data representative of the peripheral edge of the grain kernel by processing said sample image data in said data processing device;

determining germ edge data representative of the peripheral edge of the germ of the grain kernel by processing said sample image data in said data processing device;

comparing said kernel and germ edge data to standard edge data received from a memory storage medium associated with said data processing device and representative of at least one known cultivar of grain;

identifying said grain sample as said known cultivar if said kernel and germ edge data matches said standard edge data according to predetermined correlation criteria;

determining if said kernel edge data includes edge data corresponding to inclusions in said kernel; and processing said kernel edge data to interpolate hypothetical edge data representative of an undamaged edge of said kernel when said kernel edge data includes edge data corresponding to inclusions in said kernel.

2. A method of identifying the cultivar of a grain sample according to claim 1 including the step of processing said kernel edge data to provide cartesian coordinate data representative of and derived from said kernel edge data.

3. A method of identifying the cultivar of a grain sample according to claim 1 including the step of processing said germ edge data to provide cartesian coordinate data representative of and derived from said germ edge data.

4. A method of identifying the cultivar of a grain sample according to claim 1 including the step of determining the area of the kernel.

5. A method of identifying the cultivar of a grain sample according to claim 4 including the step of determining the perimeter of the kernel.

6. A method of identifying the cultivar of a grain sample according to claim 4 including the step of determining the centroid of the kernel.

7. A method of identifying the cultivar of a grain sample according to claim 5 including the step of determining the principal axes of the kernel.

8. A method of identifying the cultivar of a grain sample according to claim 5 including the step of determining the area of the germ.

9. A method of identifying the cultivar of a grain sample according to claim 8 including the step of determining the perimeter of the germ.

10. A method of identifying the cultivar of a grain sample according to claim 9 including the step of determining the centroid of the germ.

11. A method of identifying the cultivar of a grain sample according to claim 9 including the step of determining the principal axes of the germ.

12. A method of identifying the cultivar of a grain sample according to claim 5 including the step of determining the ratio between the area of the kernel and the perimeter of the kernel.

13. A method of identifying the cultivar of a grain sample according to claim 5 including the step of determining the length of the kernel and the breadth of the kernel, and including the step of determining the ratio between the length of the kernel and the breadth of the kernel.

14. A method of identifying the cultivar of a grain sample according to claim 5 including the step of determining the formfactor of the kernel.

15. A method of identifying the cultivar of a grain sample according to claim 5 including the step of determining the length of the kernel and the breadth of the kernel, and including the step of determining the rectangularity factor of the kernel.

16. A method of identifying the cultivar of a grain sample according to claim 9, including the step of determining the ratio between the area of the germ and the perimeter of the germ.

17. A method of identifying the cultivar of a grain sample according to claim 9 including the step of determining the length of the germ and the breadth of the germ, and including the step of determining the ratio between the length of the germ and the breadth of the germ.

18. A method of identifying the cultivar of a grain sample according to claim 5 including the step of determining the formfactor of the germ.

19. A method of identifying the cultivar of a grain sample according to claim 9 including the step of determining the length of the germ and the breadth of the germ, and including the step of determining the rectangularity factor of the germ.

20. A method of identifying the cultivar of a grain sample according to claim 9 including the step of determining the ratio of the kernel area to the germ area.

21. A method of identifying the cultivar of a grain sample according to claim 9 including the step of determining the ratio of the kernel perimeter to the germ perimeter.

22. A method of identifying the cultivar of a grain sample according to claim 9, including the step of determining the kernel breadth and the germ breadth and the step of determining the ratio between the kernel breadth and the germ breadth.

23. A method of identifying the cultivar of a grain sample according to claim 9, including the step of determining the kernel length and the germ length and the step of determining the ratio between the kernel length and the germ length.

24. A method of identifying the cultivar of a grain sample according to claim 1 wherein said standard edge data includes the perimeter of a kernel of said known cultivar of grain.

25. A method of identifying the cultivar of a grain sample according to claim 1 wherein said standard edge data includes the area of a kernel of said known cultivar of grain.

26. A method of identifying the cultivar of a grain sample according to claim 1 wherein said standard edge data includes the length of a kernel of said known cultivar of grain.

27. A method of identifying the cultivar of a grain sample according to claim 1 wherein said standard edge data includes the breadth of a kernel of said known cultivar of grain.

28. A method of identifying the cultivar of a grain sample according to claim 1 wherein said standard edge data includes the perimeter of a germ of said known cultivar of grain.

29. A method of identifying the cultivar of a grain sample according to claim 1 wherein said standard edge data includes the area of a germ of said known cultivar of grain.

30. A method of identifying the cultivar of a grain sample according to claim 1 wherein said standard edge data includes the length of a germ of said known cultivar of grain.

31. A method of identifying the cultivar of a grain sample according to claim 1 wherein said standard edge data includes the breadth of a germ of said known standard of grain.

32. A method of identifying the cultivar of a grain sample according to claim 1 wherein said standard edge data includes data representative of a plurality of known cultivars of grain.

33. A method of identifying the cultivar of a grain sample according to claim 1 wherein said standard edge data includes a range of data corresponding to a predetermined number of standard deviations from a statistical norm for edge data representative of a known cultivar of grain.

34. A method of identifying the cultivar of a grain sample according to claim 1 wherein said grain sample includes a plurality of kernels of grain, each kernel including a germ therein, and including the step of determining a statistical norm and distribution therefrom of the kernel edge data and the germ edge data in said data processing device.

35. A method of identifying the cultivar of a grain sample according to claim 34, wherein said identifying step comprises matching the statistical norm and distribution of the grain sample against the statistical norm and distribution of said known cultivar of grain.

36. A method of identifying the cultivar of a grain sample according to claim 1, wherein said grain sample includes a plurality of cultivars of grain, and including the step of identifying the grain sample as a mixed sample if the kernel and germ edge data of said sample is representative of more than one known cultivar of grain when matched against standard edge data according to predetermined correlation criteria.

37. A method of identifying the cultivar of a grain sample according to claim 36, including the step of identifying the known cultivars comprising the mixed cultivar grain sample.

38. A method of identifying the cultivar of a grain sample according to claim 1, wherein said grain sample includes a plurality of cultivars of grain, and including the step of identifying the grain sample as a mixed sample if the kernel and germ edge data of said sample is representative of one known cultivar of grain and one unknown cultivar of grain when match against standard edge data according to predetermined correlation criteria.

39. A method of identifying the cultivar of a grain sample according to claim 1, wherein said kernel and germ edge data comprise a plurality of discriminators and said standard edge data comprises at least some of discriminators, said predetermined correlation criteria comprising a predetermined number of matches between said kernel and germ edge data discriminators and said standard edge data discriminator necessary to identify said grain sample as a known cultivar.

40. A method of identifying the cultivar of a grain sample according to claim 39, wherein said correlation criteria further comprises a range for each standard edge data discriminator representative of a predetermined number of standard deviations from a norm corresponding to said known cultivar for said standard edge data discriminator.

41. A method of identifying the cultivar of a grain sample according to claim 39 wherein said kernel and germ edge data includes discriminators selected from the group including kernel area, germ area, kernel perimeter, germ perimeter, kernel length, germ length, kernel breadth and germ breadth.

42. A method of identifying the cultivar of a grain sample having a kernel of grain with the kernel including a germ therein, said method comprising the steps of:

receiving sample image data representative of an image of a kernel of grain into a data processing device;

determining kernel edge data representative of the peripheral edge of the grain kernel by processing said sample image data in said data processing device;

determining germ edge data representative of the peripheral edge of the germ of the grain kernel by processing said sample image data in said data processing device;

comparing said kernel and germ edge data to standard edge data received from a memory storage medium associated with said data processing device and representative of at least one known cultivar of grain;

identifying said grain sample as said known cultivar if said kernel and germ edge data matches said standard edge data according to predetermined correlation criteria;

determining if said kernel edge data includes edge data corresponding to inclusions in said kernel; and processing said germ edge data to interpolate hypothetical edge data representative of an undamaged edge of said germ when said germ edge data includes edge data corresponding to inclusions in said germ.

43. A method of identifying the cultivar of a grain sample having a kernel of grain with the kernel including a germ therein, said method comprising the steps of:

receiving sample image data representative of an image of a kernel of grain into a data processing device;

determining kernel edge data representative of the peripheral edge of the grain kernel by processing said sample image data in said data processing device;

determining germ edge data representative of the peripheral edge of the germ of the grain kernel by processing said sample image data in said data processing device;

comparing said kernel and germ edge data to standard edge data received from a memory storage medium associated with said data processing device and representative of at least one known cultivar of grain;

identifying said grain sample as said known cultivar if said kernel and germ edge data matches said standard edge data according to predetermined correlation criteria;

determining if said germ edge data includes edge data corresponding to germ edge discontinuities; and processing said germ edge data to extrapolate hypothetical edge data representative of a projected edge of said germ when said germ edge data includes edge data corresponding to germ edge discontinuities.

44. Apparatus for identifying a grain sample having a grain with the kernel including a germ therein comprising:

means for acquiring an image of a grain sample including the images of the kernel and germ thereof;

means operatively connected to said image acquisition means for converting the acquired germ and kernel images to image data in digital format;

data processing means operatively connected to said conversion means for processing said image data to identify edge data representative of the edge of the kernel image and the edge of the germ image, for storing standard edge data representative of a known cultivar of grain, and for comparing said edge data to said standard edge data;

means for determining if said kernel edge data includes edge data corresponding to inclusions in said kernel; and means for interpolating hypothetical edge data representative of an undamaged edge of said kernel when said kernel edge data includes edge data corresponding to inclusions in said kernel.

45. Apparatus for identifying a grain sample having a grain with the kernel including a germ therein comprising:

means for acquiring an image of a grain sample including the images of the kernel and germ thereof;

means operatively connected to said image acquisition means for converting the acquired germ and kernel images to image data in digital format;

data processing means operatively connected to said conversion means for processing said image data to identify edge data representative of the edge of the kernel image and the edge of the germ image, for storing standard edge data representative of a known cultivar of grain, and for comparing said edge data to said standard edge data;

means for determining if said kernel edge data includes edge data corresponding to inclusions in said kernel; and means for interpolating hypothetical edge data representative of an undamaged edge of said germ when said image data includes germ edge data corresponding to inclusions in said germ.

46. Apparatus for identifying a grain sample having a grain with the kernel including a germ therein comprising:

means for acquiring an image of a grain sample including the images of the kernel and germ thereof;

means operatively connected to said image acquisition means for converting the acquired germ and kernel images to image data in digital format;

data processing means operatively connected to said conversion means for processing said image data to identify edge data representative of the edge of the kernel image and the edge of the germ image, for storing standard edge data representative of a known cultivar of grain, and for comparing said edge data to said standard edge data;

means for determining if said image data includes germ data corresponding to germ edge discontinuities; and means for extrapolating hypothetical edge data representative of a projected edge of said germ when said image data includes germ edge data corresponding to germ edge discontinuities.

47. A method of identifying the cultivar of a grain sample according to claim 1, wherein said grain sample is a wheat sample.

48. A method of identifying the cultivar of a grain sample according to claim 1, wherein said sample image data is received in digital format.

49. A method of identifying the cultivar of a grain sample according to claim 48, wherein said sample image data is converted into digital format by processing in an analog to digital converter.

50. A method of identifying the cultivar of a grain sample according to claim 1 including the step of acquiring an image of the kernel of grain by an image acquisition device.

51. A method of identifying the cultivar of a grain sample according to claim 50 including the step of backlighting the grain sample prior to acquiring the image.

52. A method of identifying the cultivar of a grain sample according to claim 50 including the step of toplighting the grain sample prior to acquiring the image.

53. A method of identifying the cultivar of a grain sample according to claim 50 wherein said image acquisition device comprises a videocamera and including the step of resolving an image of said kernel of grain received by said videocamera into said sample image data in pixel format.

54. A method of identifying the cultivar of a grain sample according to claim 53, wherein said kernel edge determining step includes processing said sample image data into a binary value matrix corresponding to said sample image data and representative of the image of said kernel.

55. A method of identifying the cultivar of a grain sample according to claim 54, wherein said kernel edge determining step includes further processing of said sample image data to change the value of said sample image data representative of the interior of the kernel to a value in said binary value matrix equal to the value of the image data representative of the area surrounding the edge of the kernel and different from the value of the image data representative of the edge of the kernel.

56. A method of identifying the cultivar of a grain sample according to claim 55, wherein said kernel edge determining step includes the step of establishing a brightness level threshold for said sample image data for differentiating between sample image data corresponding to said kernel and sample image data corresponding to the area of the image surrounding said kernel.

57. A method of identifying the cultivar of a grain sample according to claim 54, wherein said germ edge determining step includes processing said sample image data into a binary value matrix corresponding to said sample image data and representative of the image of said kernel.

58. A method of identifying the cultivar of a grain sample according to claim 57, wherein said germ edge determining step includes further processing of said sample image data to change the value of said sample image data representative of the interior of the germ to a value in said binary value matrix equal to the value of the image data representative of the area surrounding the edge of the germ and different from the value of the image data representative of the edge of the germ.

59. A method of identifying the cultivar of a grain sample according to claim 57, wherein said germ edge determining step includes the step of establishing a brightness level threshold for said sample image data for differentiating between sample image data corresponding to said germ and sample image data corresponding to the area of the image surrounding said germ.

60. Apparatus for identifying a grain sample as set forth in claim 44, including an output device for generating signals to report the results of said comparison between said edge data and said standard edge data.

61. Apparatus for identifying a grain sample as set forth in claim 60 wherein said output device includes a video monitor.

62. Apparatus for identifying a grain sample as set forth in claim 44 wherein said image acquiring means includes a video camera.

63. Apparatus for identifying a grain sample as set forth in claim 62 wherein said image acquiring means includes a microscope.

64. Apparatus for identifying a grain sample as set forth in claim 44 including means for illuminating said grain sample.

65. Apparatus for identifying a grain sample as set forth in claim 44 wherein said data processing means includes means for storing said edge data in a retrievable matrix.

66. Apparatus for identifying a grain sample as set forth in claim 44 wherein said data processing means includes means for processing said image data into a binary matrix representative of the image of the kernel or germ of said grain sample.

67. Apparatus for identifying a grain sample as set forth in claim 44, said grain sample comprising a plurality of kernels, said data processing means including means for developing a statistical distribution of said edge data representative of grain identification discriminators for grain sample.

68. Apparatus for identifying a grain sample as set forth in claim 44, wherein said image processing means includes means for establishing a brightness threshold to identify the image data representative of the kernel of said grain sample.

69. Apparatus for identifying a grain sample as set forth in claim 68, wherein said grain sample comprises a plurality of kernels, said brightness threshold establishing means functioning to independently establish a brightness threshold for each kernel.

70. Apparatus for identifying a grain sample as set forth in claim 44, wherein said image processing means includes means for establishing a brightness threshold to identify the image data representative of the germ of said grain sample.

71. Apparatus for identifying a grain sample as set forth in claim 70, wherein said grain sample comprises a plurality of kernels, said brightness threshold establishing means functioning to independently establish a brightness threshold for each germ.

* * * * *